United States Patent [19]

Orphanides

[11] 4,154,737

[45] May 15, 1979

[54] PREPARATION OF MALEIMIDES AND DIMALEIMIDES

[75] Inventor: Gus G. Orphanides, Newark, Del.

[73] Assignee: E. I. Du Pont de Nemours and Company, Wilmington, Del.

[21] Appl. No.: 777,319

[22] Filed: Mar. 14, 1977

Related U.S. Application Data

[63] Continuation-in-part of Ser. No. 683,398, May 5, 1976, abandoned.

[51] Int. Cl.$^2$ ............... C07D 403/10; C07D 403/08; C07D 207/40
[52] U.S. Cl. .................. 260/326.26; 260/326.5 FM
[58] Field of Search .............. 260/326.5 FM, 326.26

[56] References Cited

U.S. PATENT DOCUMENTS

| | | | |
|---|---|---|---|
| 2,180,694 | 4/1961 | Sauers | 260/326.5 |
| 2,965,553 | 12/1960 | Dixon et al. | 204/154 |
| 2,989,504 | 6/1961 | Little | 260/62 |
| 3,334,075 | 8/1967 | Kehn | 260/85.3 |
| 3,522,271 | 7/1970 | Kalil | 260/326.26 |
| 3,669,930 | 6/1972 | Asahara et al. | 260/47 CZ |
| 3,839,358 | 10/1974 | Bargain | 260/326.26 |
| 3,878,224 | 4/1975 | Kasagai | 260/326 R |
| 3,933,850 | 1/1976 | Ladd | 260/326.26 |
| 3,948,942 | 4/1976 | Debourge et al. | 260/326.5 FM |
| 3,960,887 | 6/1976 | Renard | 260/326.5 FM |
| 3,975,401 | 8/1976 | Balmé | 260/326.26 |

FOREIGN PATENT DOCUMENTS

2454856  5/1975  Fed. Rep. of Germany.

OTHER PUBLICATIONS

Naumov et al., Chem. Abs. 75, 87793f (1971).
Rubber Technology and Manufacture, Blow, Editor, CRC Press, 1971, pp. 189-192.
F. Albert Cotton, Adv. Inorg. Chem., 3rd Ed. pp. 190, 191, 201, 202, 216-221.
Rubber Technology, M. Morton, 2nd Edition, Van Norstrand Reinhold.

*Primary Examiner*—Mark L. Berch

[57] ABSTRACT

A process for the preparation of maleimides and dimaleimides in high yield, wherein in the first step maleic anhydride and a suitable primary amine or diamine are contacted at about 30°-60° C. in the presence of a simple, cheap organic solvent; and in the second step the thus-formed intermediate is cyclized, without prior isolation, at 45°-60° C. in the presence of a lower fatty acid anhydride, a tertiary amine having a $pK_a$ of at least 10 and of a salt of magnesium, lithium, manganese(II), or cobalt(II) soluble in the liquid reaction medium to the extent of at least 0.2 weight percent. Alternatively, the tertiary amine can be added in the first step. The product maleimide or dimaleimide normally can be isolated by filtration after cooling to room temperature. Water-miscible solvents may be diluted with water prior to product isolation. Certain N,N'-arylene-dimaleimides, which can be prepared by this process, are vulcanization adjuvants for elastomers.

14 Claims, No Drawings

PREPARATION OF MALEIMIDES AND DIMALEIMIDES

CROSS-REFERENCE TO RELATED APPLICATION

This is a continuation in part of my copending application Ser. No. 683,398, filed May 5, 1976, now abandoned.

BACKGROUND OF THE INVENTION

Certain N,N'-arylenedimaleimides, particularly N,N'm-phenylenedimaleimides, have long been known as vulcanization adjuvants for elastomers. The ortho- meta-, and para- isomers of N,N'-arylenedimaleimides are prepared by reacting an arylenediamine and maleic anhydride in the presence of a polar organic solvent to form an N,N'-aryldimaleamic acid precursor, and dehydrating the latter by ring closure with a lower fatty acid anhydride and an alkali metal salt of a lower fatty acid to form the corresponding dimaleimide.

A typical example of this process is the formation of N,N'-m-phenylenedimaleimide. This involves the addition of maleic anhydride to a solution of m-phenylenediamine in dimethylformamide (DMF) and reacting these at a temperature of 35°–40° C. to form N,N'-m-phenylenedimaleamic acid, which is not isolated. The addition of sodium acetate and acetic anhydride follows, with a maximum reaction temperature for ring closure of 55°–60° C. On the completion of this reaction, a large excess of water is added, precipitating the N,N'-m-phenylenedimaleimide which is subsequently filtered, washed with water, and dried at a moderately elevated temperature. This process is outlined below:

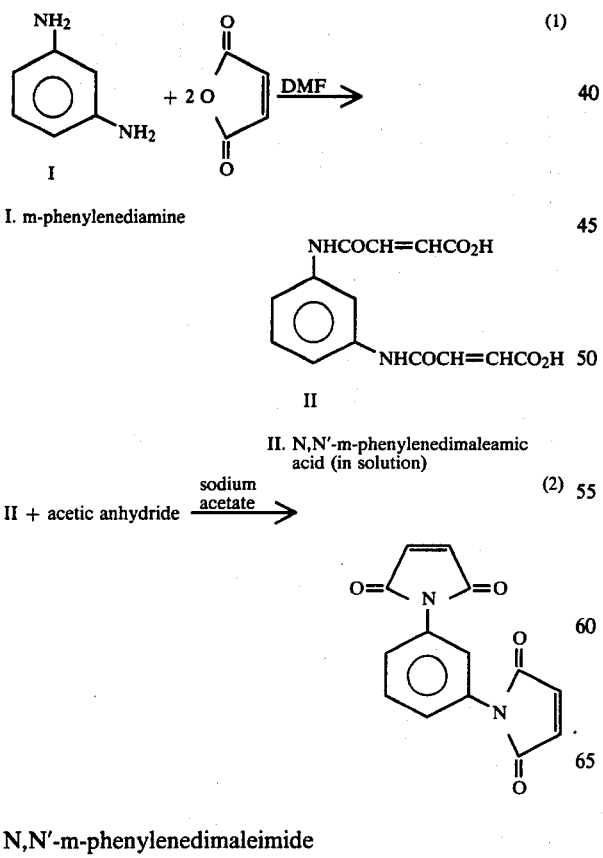

I. m-phenylenediamine

II. N,N'-m-phenylenedimaleamic acid (in solution)

N,N'-m-phenylenedimaleimide

This process is plagued by low yields (60–65%) and a product isolation process which requires large amounts of water to precipitate the end product. However, the problem posing the greatest economic and ecological concern for this process is the conversion of the necessary expensive and moderately toxic DMF solvent by acetic acid to large amounts of dimethylacetamide and formic acid during the reaction. The consumption of solvent necessitates expensive disposal measures in order to meet standards for environmental quality, since about three to four parts of DMF are consumed and thus discarded per one part of end product. The low solubility of the dimaleamic acid aggravates this problem by requiring large amounts of solvent. Moreover, one must avoid extremes of temperature in the ring-closure step (less than 40° C. or greater than 65° C.) in order to enhance the reaction rate and the solubility of the dimaleamic acid without destroying significant amounts of the dimaleamic acid via side reactions that become prominent at higher temperatures. One desirable product, N,N'-(4-methyl-m-phenylene) dimaleimide, cannot be easily isolated when DMF is used as solvent.

Attempts have been made in the past to employ alternative solvent systems. Use of formamide instead of DMF also resulted in the reaction of the solvent with the acetic acid generated, while giving poorer yields and requiring increased amounts of sodium acetate. Processes using different solvents for the two different steps have been successful in the laboratory, but have proven impractical in larger scale production due to the expense and time involved in removing the first solvent before proceeding with ring-closure. An example of such a process is the synthesis of the dimaleamic acid in an aqueous solution, isolating it, and carrying out the conversion to the dimaleimide in a nonaqueous solvent. This latter reaction will not proceed in an aqueous solvent.

The aim of this invention is to provide a synthetic method for maleimides and dimaleimides which will reduce costs and decrease ecological hazards.

SUMMARY OF THE INVENTION

According to the present invention, there is now provided a process for the preparation of maleimides and dimaleimides in high yield, said process comprising the following sequential steps:

(1) contacting maleic anhydride and a suitable primary amine or diprimary diamine at about 30°–60° C. in an organic solvent selected from organic ketones, ethers, esters, and chlorinated aromatic organic hydrocarbons to form the corresponding maleamic acid or dimaleamic acid;

(2) without isolating the product of step (1), admixing the reaction mixture of step (1) with (a) about 1–1.5 moles of an anhydride of a $C_2$–$C_5$ fatty acid per equivalent of —$NH_2$ groups in the starting primary amine or diprimary diamine and (b) a hydrated or nonhydrated salt of magnesium, lithium, manganese(II), or cobalt(II) which is soluble in the liquid reaction medium at the reaction temperature to the extent of at least 0.2 weight percent, and maintaining with adequate agitation at about 45°–60° C.; and (3) recovering the maleimide or dimaleimide product; with the proviso that a tertiary amine having $pK_a$, determined in aqueous solution at 25° C., of at least 10, also is present either in step (1) or in step (2).

DEFINITION

For the purpose of the present invention, "liquid reaction medium" is defined as the combination of
(a) the selected organic solvent
(b) the tertiary amine, and
(c) the fatty acid anhydride introduced in step (2) of the process.

DETAILED DESCRIPTION OF THE INVENTION

The main advantage of the present invention resides in the use of cheap organic solvents which can be disposed of or totally recovered after the reaction without creating any serious ecological hazards. The tertiary amine may also be recovered. Suitable reaction solvents are, among others, acetone, cyclohexanone, dioxane, tetrahydrofurane, methyl ethyl ketone, ethyl acetate, and o-dichlorobenzene. It is advisable to select a solvent which dissolves maleic anhydride reasonably well. The particularly preferred solvent is acetone.

The primary amine or diprimary diamine used in the first step of this process can be any alkylamine, cycloalkylamine, arylamine, or aralkylamine, preferably having no more than 12 carbon atoms; any alkylenediamine, preferably having 2–12 carbon atoms, $C_4$–$C_{12}$ cycloalkylenediamine, arylenediamine, or alkylenebis(arylamine). The aryl or cycloalkyl rings may be further substituted with $C_1$–$C_9$ alkyl or alkoxy groups or Cl, Br, or F atoms. Aromatic and cycloaliphatic diamines may be o-, m-, or p-diamines. Of particular interest are m-phenylenediamine, 4-methyl-m-phenylenediamine, methylene-p,p'-dianiline, 1,4-di(aminomethyl)cyclohexane, and 1,4-di($\beta$-aminoethyl)cyclohexane. The preferred aromatic monoamine is aniline.

Suitable metal salts which catalyze the dehydration cyclization step include, for example, magnesium nitrate, chloride, bromide, sulfate and acetate; lithium nitrate, chloride, bromide and acetate; manganese (II) nitrate, chloride, and acetate and cobalt (II) nitrate, chloride, bromide, sulfate, and acetate.

The dehydration (cyclization) step is carried out in the same reaction mixture, without isolating the intermediate. This is one of the advantages of the present process. While cyclization in the presence of a tertiary amine and a lower fatty acid anhydride is known to the art, the presence of a selected metal salt according to the process of the present invention results in much higher yields of the desired product. It is believed that both the tertiary amine and the metal salt act as co-catalysts in this step, a synergistic effect being produced. Suitable anhydrides of $C_2$–$C_5$ fatty acids are acetic, propionic, and all isomeric forms of butyric and valeric anhydrides. Acetic anhydride, which is the most readily available, is preferred. Optimum yields are obtained when about 1.2–1.4 moles of the anhydride per equivalent of —$NH_2$ groups in the primary amine or diprimary diamine are used. It would not be advantageous to increase the amount of the anhydride beyond about 1.5 moles per —$NH_2$ group equivalent. Any tertiary amine which has a sufficiently high $pK_a$ is suitable in the process of this invention. Typical amines include triethylamine, tributylamine, N,N-diethylcyclohexylamine, N-methylpiperidine, and 1,4-diazabicyclo[2.2.2]octane.

While it is theoretically sufficient to have only a catalytic amount of the tertiary amine present in the reaction mixture, it has been found advantageous to use a rather large amount of this amine to improve the solubility of the intermediate maleamic or dimaleamic acid. The proportion of the tertiary amine may be as high as 60 mole percent of primary amine, and even higher, but often an amount of about 30 mole percent will be adequate. It is not recommended to use less than about 15 mole percent.

The preferred temperature range for the first step of the process is about 35°–45° C., which is maintained for about one-half hour. Temperatures lower than those given in the Summary Of The Invention for each step of the process are impractical because of low reaction rates and low solubility of starting materials and/or reaction products. Higher temperatures than the upper ranges given usually yield products of lower quality. Under the preferred temperature conditions, both steps are taking place at practical reaction rates and give high quality products.

Recovery of the maleimide or dimaleimide product is simple since usually a major part thereof precipitates on cooling the reaction mixture to room temperature. In the case of water-miscible solvents, additional product can be recovered by diluting the mixture with water prior to the filtration step. When the solvent is not miscible with water, the yield of the recovered maleimide or dimaleimide can often be increased by cooling the reaction mixture to about 0° C. prior to filtration.

The quantity of solvent required to operate the present process in commercial equipment cannot be specified exactly as it depends on the particular solvent and the maleimide or dimaleimide being prepared as well as such factors as temperature and the concentration of the tertiary alkylamine. In general, however, 2 to 12 parts by weight of solvent per part of the expected maleimide or dimaleimide product are sufficient to provide a readily workable reaction mixture medium throughout both steps of the syntheses. In the case of N,N'-m-phenylene- and N,N'-(4-methyl-m-phenylene)dimaleimides, a process using about 3 parts of acetone per part of the expected dimaleimide gives good operability high productivity and good product quality. The mole ratio of tertiary alkylamine to the starting primary amine or diamine is ordinarily 0.05 to 0.8. The mole ratio of metal salt to the starting primary amine or diamine is ordinarily 0.01 to 0.20.

As compared to previous syntheses, particularly those using DMF solvent, the process of this invention produces a much higher yield of dimaleimide product and one of high purity. For example, N,N'-m-phenylenedimaleimide as produced by the process of this invention is a brighter yellow than produced by using the prior art DMF method, indicating higher purity, which is further evidenced by its melting point of at least 200° C., usually 202°–205° C. By contrast, prior art processes often produce products having melting points below 200° C. or greater than 210° C., both of which have been found to be unsatisfactory in commercial use.

In the following illustrative examples, all parts, proportions, and percentages are by weight unless otherwise indicated. All melting points are uncorrected.

EXAMPLE 1

This example illustrates various metal salt co-catalysts that may be used to prepare N,N'-m-phenylenedimaleimide.

A glass flask was equipped with a thermometer, mechanical paddle stirrer and a water cooled condenser.

Crushed maleic anhydride (1.92 parts) was added to a solution of 1 part m-phenylenediamine and 13 parts acetone over a 15-minute period. The heterogeneous reaction mixture was stirred at 40° C. for 1 hour. Acetic anhydride (2.44 parts), 0.32 part triethylamine, and 0.04 part magnesium acetate tetrahydrate were added all at once. The temperature was raised to 60° C. using a heating mantle and maintained for 4 hours. The reaction mixture was cooled, 20 parts water added, and the precipitated product isolated by filtration using a vacuum filter funnel. The filter cake was washed with water and dried for 24 hours at 60°–70° C. in a vacuum oven. A 74% yield of N,N'-m-phenylenedimaleimide, m.p. 203°–204° C. was obtained.

The example was repeated except that 0.04 part lithium acetate dihydrate was used as the catalyst instead of magnesium acetate tetrahydrate. N,N'-m-phenylenedimaleimide, m.p. 208° C., was obtained in 84% yield.

The example was repeated except that 0.04 part manganous acetate tetrahydrate was used as catalyst instead of magnesium acetate tetrahydrate. N,N'-m-phenylenedimaleimide, m.p. 203°–204° C., was obtained in 80% yield.

The example was repeated except that 0.02 part lithium chloride was used as catalyst instead of magnesium acetate tetrahydrate. N,N'-m-phenylenedimaleimide, m.p. 199° C., was obtained in 84% yield.

EXAMPLE 2

This example illustrates various metal salt and amine cocatalysts that may be used to prepare N,N'-m-phenylenedimaleimide.

A flask was equipped as in Example 1. To a solution of maleic anhydride (1.92 parts) in 4.8 parts acetone was added a solution of 1 part m-phenylenediamine, 0.32 part triethylamine and 1.6 parts acetone over a 15-minute period. A precipitate formed during that time. The heterogeneous reaction mixture was maintained at 40° C. for 30 minutes. Magnesium chloride hexahydrate (0.08 part) and 2.44 parts acetic anhydride were added all at once. The temperature was raised to 50° C. and maintained for 3 hours. After 30 minutes, the reaction mixture became homogeneous and amber in color. Five minutes later, the product began to precipitate. At the end of the reaction time, the mixture was cooled and 12 parts water added. The precipitated product was collected by vacuum filtration, washed with water, and dried for 24 hours at 60° C. in a vacuum oven. A 92% yield of N,N'-m-phenylenedimaleimide, m.p. 204°–205° C., was obtained.

The example was repeated except 0.1 part magnesium sulfate heptahydrate was used in place of 0.08 part magnesium chloride hexahydrate. An 89% yield of N,N'-m-phenylenedimaleimide, m.p. 206°–207° C., was obtained.

The example was repeated except 0.5 part N,N-diethylcyclohexylamine was used in place of 0.32 part triethylamine. A 92% yield of N,N'-m-phenylenedimaleimide, m.p. 202°–203° C., was obtained.

EXAMPLE 3

This example illustrates the use of 4-methyl- and 2-methyl-m-phenylenediamine in the preparation of aryl-dimaleimides.

A flask was equipped as in Example 1. To a solution of maleic anhydride (1.7 parts) in 3.9 parts acetone was added a solution of 1 part 4-methyl-m-phenylenediamine, 0.28 part triethylamine and 2.5 parts acetone. The heterogeneous reaction mixture was stirred at 40° C. for 30 minutes. Magnesium chloride hexahydrate (0.071 part) and 2.16 part acetic anhydride were added all at once. The reaction temperature was raised to 50° C. and maintained for 2.5 hours. Thirty minutes after the addition the mixture became homogeneous and remained so. The solution was cooled, and 16 parts water was added; the precipitated product was filtered by vacuum filtration, washed with water, and dried in a vacuum oven at 60° C. for 24 hours. N,N'-(4-Methyl-m-phenylene)-dimaleimide, m.p. 168°–172° C., was obtained in 85% yield.

The example was repeated except 1 part 2-methyl-m-phenylenediamine was used in place of 1 part 4-methyl-m-phenylenediamine. The diamine was added to the vessel as a solution containing 0.28 part triethylamine and 3.2 parts acetone. N,N'-(2-methyl-m-phenylene)-dimaleimide, m.p. 210°–212° C., was obtained in 85% yield.

EXAMPLE 4

This example illustrates the use of various alkyl and aromatic mono- and difunctional amines in the preparation of maleimides.

A flask was equipped as in Example 1. To a solution of maleic anhydride (1.06 parts) in 3.5 parts acetone was added a mixture of 1 part methylenedianiline, 0.35 part triethylamine and 1.0 part acetone over a 30-minute period. A precipitate formed during that time. The heterogeneous reaction mixture was maintained at 40° C. for 30 minutes. Magnesium chloride hexahydrate (0.044 part) and 1.34 parts acetic anhydride were added all at once. The reaction mixture was stirred at 45° C. for 5–6 hours. Fifteen minutes after the addition, the mixture became homogeneous and remained so. The solution was cooled and 5.5 parts water added. The precipitated product was isolated by vacuum filtration, washed with water, and dried. An 89% yield of N,N'-(methylenedi-p-phenylene)dimaleimide, m.p. 154°–155° C. was obtained.

A flask was equipped as in Example 1. To a solution of maleic anhydride (3.64 parts) in 10.6 parts acetone was added a solution of 1 part ethylenediamine, 0.61 part triethylamine and 1.5 parts acetone over a 25-minute period. The resulting reaction mixture contained white solids and was maintained at 40° C. for 30 minutes. Magnesium chloride hexahydrate (0.15 part) and 4.6 parts acetic anhydride were added all at once. The reaction temperature was raised to 50° C. and held there for 2.5 hours. The homogeneous reaction mixture was cooled and 25 parts water added. The precipitated product was filtered by vacuum filtration, washed with water, and dried in a vacuum oven. A 27% yield of N,N'-ethylenedimaleimide, m.p. 193°–194° C., was obtained.

A flask was equipped as in Example 1. To a solution of maleic anhydride (1.8 parts) in 5.2 parts acetone was added a solution of 1 part hexamethylenediamine, 0.3 part triethylamine and 1.5 parts acetone over a 30-minute period. The resulting heterogeneous reaction mixture was maintained at 40°–50° C. for 30 minutes. Magnesium chloride hexahydrate (0.075 part) and 2.3 parts acetic anhydride were added all at once. The reaction mixture was maintained at 50° C. for 3 hours. Water (11 parts) was added to the cooled mixture and the precipitated product isolated by vacuum filtration.

The filter cake was washed with water and dried in a vacuum oven. A 22% yield of N,N'-hexamethylenedimaleimide, m.p. 136°-139° C., was obtained.

A reaction flask was equipped as in Example 1. To a solution of maleic anhydride (1.12 parts) in 5.6 parts acetone was added a solution of 1 part aniline, 0.375 part triethylamine, and 1.9 parts acetone over a 30-minute period. The resulting heterogeneous mixture was maintained at 40° C. for 30 minutes. Magnesium chloride hexahydrate (0.093 part) and 1.4 parts acetic anhydride were added all at once. The temperature was raised to 50° C. for 3 hours. The homogeneous mixture was cooled and 14 parts water added. The precipitated product was isolated by vacuum filtration, washed with water, and air dried. The crude product was recrystallized from ethanol/water (90/10 vol.) to yield 0.89 part N-phenyl maleimide, m.p. 84°-86° C.

EXAMPLE 5

This example illustrates the use of a different solvent.

A flask was equipped as in Example 1. To a solution of maleic anhydride (1.92 parts) and 13 parts ethyl acetate was added a mixture of 1 part m-phenylenediamine, 0.32 part triethylamine and 2.3 parts ethyl acetate over a 40-minute period. The resulting heterogeneous mixture was maintained at 40° C. for 50 minutes. Magnesium chloride hexahydrate (0.08 part) and 2.44 parts acetic anhydride were added all at once. The temperature was raised to 50° C. and maintained for 3 hours. The precipitated product was isolated by vacuum filtration, the filter cake washed with water, and dried. A 70% yield of N,N'-m-phenylenedimaleimide, m.p. 202°-203° C., was obtained.

EXAMPLES 6-27

In the following examples synthesis of N,N'-m-phenylenedimaleimide was carried out under the same general conditions but in the presence of different metal salts, some of which are not within the scope of the present invention. In each case, the total yield of solid product was determined; its melting point was taken; and the yield of pure dimaleimide was calculated from liquid chromatography data. It is to be noted that the industrial goal is to make maleimides in as high a crude yield as possible, and in as high a degree of purity as possible to avoid the necessity of purifying the crude product prior to use in elastomer vulcanization recipes.

General Procedure

A glass flask was equipped with a thermometer, mechanical paddle stirrer and a water-cooled condenser. A solution of m-phenylenediamine (0.46 mole), triethylamine (0.16 mole) (except in Example 7), and 100 ml acetone was added over a 15-30 minute period to a solution of maleic anhydride (0.98 mole) in 300 ml acetone. A precipitate formed during that time. The heterogeneous reaction mixture was maintained at 40° C. for 30 minutes. The metal salt (0.1 or 0.01 mole per 1 mole of the diamine) and acetic anhydride (1.2 moles) were added all at once and the temperature raised to 50° C. and maintained for 3 hours. At this time 300 ml water were added and the mixture was cooled. The precipitated product was collected by vacuum filtration, washed with water and dried for 12 hours at 60° C. in a vacuum oven. The yields of recovered solids and N,N'-m-phenylenedimaleimide, based on m-phenylenediamine, obtained are shown in the tables. Liquid chromatographic yield data for the dimaleimide are accurate to ±4%. The results are presented in Table 1.

TABLE 1[a]

| Example | Metal Salt & Salt/diamine Mole Ratio | mp °C. | % yield solids | % yield Dimaleimide |
|---|---|---|---|---|
| 6 | None | 184-200 | 68 | 29 |
|  |  | 190-205 | 69 | 30 |
| 7[b] | LiOAc . 2H$_2$O (0.10) | 170-201 | 20 | 9 |
| 8 | LiOAc . 2H$_2$O (0.10) | 200-2 | 86 | 85 |
|  |  | 201-3 | 87 | 85 |
| 9 | NaOAc (0.10)(c) | 195-202 | 72 | 68 |
|  |  | 197-203 | 72 | 68 |
| 10 | KOAc (0.10)(c) | 181-195 | 59 | 34 |
|  |  | 180-197 | 62 | 40 |
| 11 | Mn(OAc)$_2$ . 4H$_2$O (0.10) | 203-5 | 88 | 84 |
|  |  | 202-4 | 88 | (d) |
| 12 | Cu(OAc)$_2$ . H$_2$O (0.10)(c) | 199-203 | 67 | 65 |
|  |  | 203-204 | 68 | 65 |
| 13 | Zn(OAc)$_2$ . 2H$_2$O (0.10)(c) | 206-7 | 56 | 52 |
|  |  | 202-8 | 56 | 54 |
| 14 | Fe(OAc)$_2$ (0.10)(c) | 196-202 | 85 | 72 |
| 15 | Co(OAc)$_2$ . 4H$_2$O (0.10) | 204-6 | 91 | 91 |
|  |  | 205-6 | 90 | (d) |
| 16 | Mn(OAc)$_2$ . 4H$_2$O (0.01) | 203-4 | 88 | 80 |
| 17 | Cu(OAc)$_2$ . H$_2$O (0.01)(c) | 195-206 | 59 | (d) |
|  |  | 195-201 | 63 | 47 |
| 18 | Zn(OAc)$_2$ . 2H$_2$O (0.01)(c) | 197-200 | 58 | 26 |
| 19 | Fe(OAc)$_2$ (0.01)(c) | 190-210 | 74 | 30 |
| 20 | Co(OAc)$_2$ . 4H$_2$O (0.01) | 203-204 | 88 | 86 |
| 21 | Co(NO$_3$)$_2$ . 6H$_2$O (0.10) | 202-3 | 89 | 89 |
| 22 | CoSO$_4$ . 7H$_2$O (0.10) | 202-4 | 89 | 89 |
| 23 | CoCl$_2$ . 6H$_2$O (0.10) | 202-3 | 88 | 87 |
| 24 | CoBr$_2$ . 6H$_2$O (0.10) | 202-4 | 87 | 84 |
| 25 | LiNO$_3$ (0.10) | 200-3 | 85 | 81 |
| 26 | Mg(NO$_3$)$_2$ . 6H$_2$O (0.10) | 200-3 | 84 | 81 |
| 27 | Mn(NO$_3$)$_2$ . 4H$_2$O (0.10) | 201-2 | 84 | 81 |

(a) - Where duplicate runs were made, two sets of results are given
(b) - No triethylamine was used in this experiment
(c) - Outside the scope of this invention
(d) - Not determined The results of the above Examples 6-27 show that:
(1) Both lithium acetate in the absence of triethylamine and triethylamine alone are poor catalysts. The combination of lithium acetate and triethylamine is an effective catalyst.
(2) Lithium acetate is a much better catalyst than either sodium acetate or potassium acetate.
(3) Manganese(II) acetate and cobalt(II) acetate are excellent catalysts, much better than three other first row transition metal acetates: zinc, copper(II), and iron(II).
(4) The superiority of manganese(II) acetate and cobalt(II) acetate is particularly evident at catalyst-/diamine mole ratios of 0.01, at which zinc, copper-(II) and iron(II) salts perform very poorly.

EXAMPLES 28-36

The general procedure was the same as in Examples 6-27, except that the metal salt/diamine mole ratio was varied over a fairly broad range. The results are reported in Table 2, below.

TABLE 2[a]

| Example | Metal Salt & Salt/Diamine Mole Ratio | mp °C. | % yield solids | % yield Dimaleimide |
|---|---|---|---|---|
| 28 | LiOAc . 2H$_2$O (0.043) | 208 | 84 | (b) |
| 29 | LiCl (0.10) | 203-5 | 85 | ~80 |
|  | (0.052) | 199-202 | 80 | (b) |
| 30 | LiBr (0.10) | 203-4 | 85 | 76 |
| 31 | Mg(OAc)$_2$ . 4H$_2$O (0.04) | 200-3 | 85 | (b) |
|  | (0.043) | 202-4 | 91 | 86 |

TABLE 2(a)-continued

| Example | Metal Salt & Salt/ Diamine Mole Ratio | mp °C. | % yield solids | % yield Dimaleimide |
|---|---|---|---|---|
| 32 | MgSO$_4$ . 7H$_2$O (0.022) | 203 | 89 | (b) |
|  | (0.044) | 206-7 | 89 | 88 |
| 33 | MgCl$_2$ . 6H$_2$O (0.043) | 201-3 | 90 | 90 |
| 34 | MgBr$_2$ . 6H$_2$O (0.043) | 202-3 | 92 | 77 |
| 35 | Mn(OAc)$_2$ . 4H$_2$O (0.018) | 203-4 | 79 | (b) |
| 36 | MnCl$_2$ (0.044) | 204-6 | 84 | 80 |

(a) - Where duplicate runs were made, two sets of results are given
(b) - Not determined The above results of Examples 28-36, in conjunction with Examples 8-27, show that high yields of N,N'-m-phenylenedimaleimide are obtained with the catalysts of the present invention irrespective of their mole ratio to the diamine, within the range tested.

I claim:

1. A process for the preparation of maleimides and dimaleimides, said process comprising the following sequential steps:
   (1) contacting maleic anhydride and a primary amine or diprimary diamine at about 30°-60° C. in an organic solvent selected from ketones, ethers, esters, and chlorinated aromatic hydrocarbons to form the corresponding maleamic acid or dimaleamic acid;
   (2) without isolating the product of step (1), admixing the reaction mixture of step (1) with (a) about 1-1.5 moles of an anhydride of a C$_2$-C$_5$ fatty acid per equivalent of —NH$_2$ groups in the starting primary amine or diprimary diamine, and (b) a salt, whether hydrated or not, selected from magnesium chloride, bromide, sulfate, and acetate, and maintaining with adequate agitation at about 45°-60° C.; and
   (3) recovering the maleimide or dimaleimide product;
   with the provisos that: I) a tertiary amine having a pK$_a$, determined in aqueous solution at 25° C., of at least 10, also is present either in step (1) or in step (2); and II) the primary amine is selected from alkylamines, cycloalkylamines, arylamines, and aralkylamines; and the diprimary diamine is selected from alkylenediamines, cycloalkylenediamines, arylenediamines, and alkylenebis(arylamines); the aryl and cycloalkyl rings of any of the above amines independently being either unsubstituted or substituted with C$_1$-C$_9$ alkyl or alkoxy groups or chlorine, bromine, or fluorine atoms.

2. The process of claim 1 wherein the amount of acid anhydride is 1.2-1.4 moles per equivalent of —NH$_2$ groups in the starting primary amine or diprimary diamine.

3. The process of claim 1 wherein the acid anhydride is acetic anhydride.

4. The process of claim 1 wherein the metal salt is magnesium sulfate.

5. The process of claim 1 wherein the temperature in step (1) is maintained at 35°-45° C.

6. The process of claim 1 wherein the mole ratio of tertiary amine to the starting primary amine or diamine is about 0.05 to 0.8, and the mole ratio of metal salt to the starting primary amine or diamine is about 0.01 to 0.20.

7. The process of claim 1 wherein the primary amine and the diprimary diamine are further limited as follows:
   the primary amine has at most 12 carbon atoms;
   when the diprimary diamine is an alkylenediamine, it has 2 to 12 carbon atoms; and
   when the diprimary diamine is a cycloalkylenediamine, it has 4-12 carbon atoms, these limitations not including any alkyl or alkoxy substituents on aryl or cycloalkyl rings.

8. The process of claim 7 wherein the starting primary monoamine is aniline.

9. The process of claim 7 wherein the starting primary diamine is m-phenylenediamine, 4-methyl-m-phenylenediamine, methylene-p,p'-dianiline, 1,4-di(aminomethyl)cyclohexane, or 1,4-di($\beta$-aminoethyl)cyclohexane.

10. The process of claim 9 wherein the solvent is acetone.

11. The process of claim 10 wherein the amount of acetone is about 3 parts by weight per part of theoretically expected dimaleimide.

12. The process of claim 1 wherein the solvent is miscible with water, and the reaction mixture is diluted with water prior to the recovery of maleimide or dimaleimide.

13. The process of claim 12 wherein the solvent is acetone.

14. The process of claim 1 wherein the tertiary amine is selected from triethylamine, tributylamine, N,N-diethylcyclohexylamine, N-methylpiperidine, and 1,4-diazabicyclo[2.2.2]octane.

* * * * *